(12) United States Patent
Akahoshi

(10) Patent No.: US 7,204,820 B2
(45) Date of Patent: Apr. 17, 2007

(54) PHACOEMULSIFICATION NEEDLE

(75) Inventor: Takayuki Akahoshi, Chiyodaku, Tokyo 101-8643 (JP)

(73) Assignees: Ravi Nallakrishnan, Westmont, IL (US); Takayuki Akahoshi, Tokyo (JP)

( * ) Notice: Subject to any disclaimer, the term of this patent is extended or adjusted under 35 U.S.C. 154(b) by 63 days.

(21) Appl. No.: 10/806,470

(22) Filed: Mar. 23, 2004

(65) Prior Publication Data

US 2004/0267211 A1    Dec. 30, 2004

Related U.S. Application Data

(63) Continuation-in-part of application No. 10/406,572, filed on Apr. 4, 2003, now abandoned.

(51) Int. Cl.
  A61F 9/00    (2006.01)
  A61B 17/32   (2006.01)
  A61B 17/20   (2006.01)
  A61M 5/00    (2006.01)
  A61M 25/00   (2006.01)

(52) U.S. Cl. .................. 604/22; 604/264; 606/107; 606/169

(58) Field of Classification Search .................. 604/22, 604/118, 119, 272, 542, 264, 257, 258, 902, 604/35; 600/459, 471; 606/169, 107
See application file for complete search history.

(56) References Cited

U.S. PATENT DOCUMENTS

| | | | |
|---|---|---|---|
| 3,809,093 A | 5/1974 | Abraham | |
| 4,767,404 A * | 8/1988 | Renton | 604/48 |
| 5,180,363 A | 1/1993 | Idemoto et al. | |
| 5,213,569 A | 5/1993 | Davis | |
| 5,464,389 A | 11/1995 | Stahl | |
| 5,527,273 A * | 6/1996 | Manna et al. | 604/22 |
| 5,653,724 A | 8/1997 | Imonti | |
| 5,718,676 A | 2/1998 | Barrett | |
| 5,741,226 A | 4/1998 | Strukel et al. | |
| 5,755,700 A | 5/1998 | Kritzinger et al. | |
| 5,989,209 A | 11/1999 | Barrett | |
| 5,993,409 A | 11/1999 | Maaskamp | |
| 6,074,396 A | 6/2000 | Geuder | |
| 6,126,629 A * | 10/2000 | Perkins | 604/22 |
| 6,159,175 A * | 12/2000 | Strukel et al. | 604/22 |
| 6,299,591 B1 | 10/2001 | Banko | |
| 6,491,670 B1 * | 12/2002 | Toth et al. | 604/264 |
| 6,533,750 B2 | 3/2003 | Sutton et al. | |

(Continued)

FOREIGN PATENT DOCUMENTS

EP    1 103 238 A1    5/2001
WO   WO 00/74615 A2  12/2000

*Primary Examiner*—Matthew DeSanto
(74) *Attorney, Agent, or Firm*—Rothwell, Figg, Ernst & Manbeck

(57) ABSTRACT

The phacoemulsification needle according to the invention comprises a shaft, a tip disposed at a distal end of said shaft, the tip having a larger outer diameter than said shaft and an aspiration lumen extending through said shaft and said tip. The tip has an opening communicating with said aspiration lumen, a ball-shaped surface and a flat distal end comprising said opening. This needle can be used for removal of the cataract nucleus as well as for removal of the residual tissue.

38 Claims, 5 Drawing Sheets

U.S. PATENT DOCUMENTS

| | | |
|---|---|---|
| 6,695,781 B2 * | 2/2004 | Rabiner et al. .............. 600/439 |
| 6,958,056 B2 | 10/2005 | Kadziauskas |
| 7,037,296 B2 | 5/2006 | Kadziauskas |
| 2002/0099325 A1 | 7/2002 | Sutton et al. |

* cited by examiner

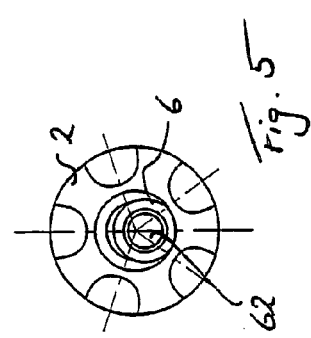
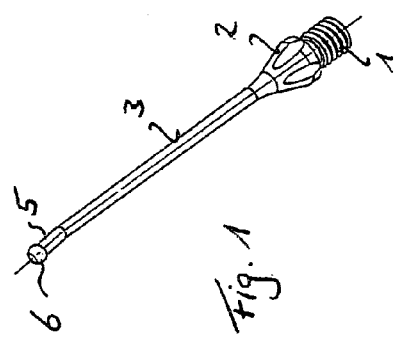
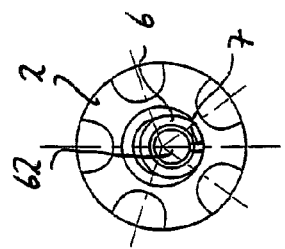
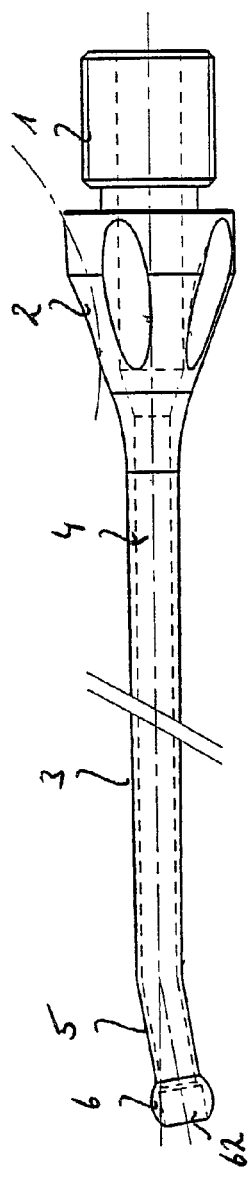
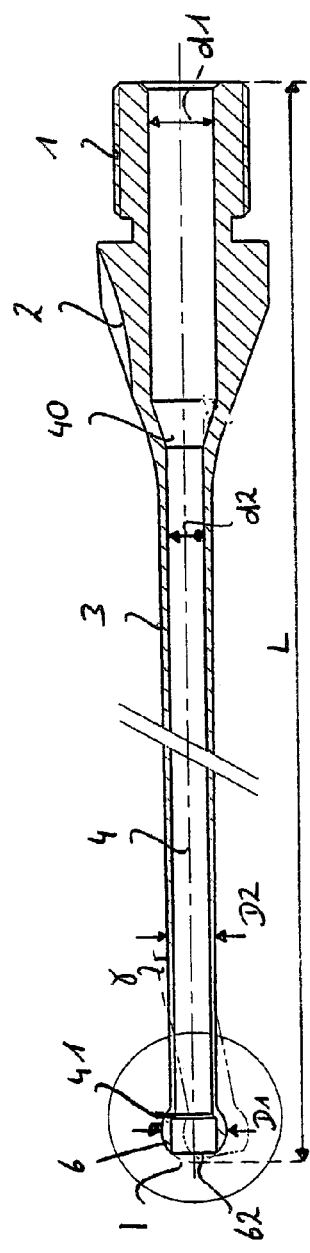
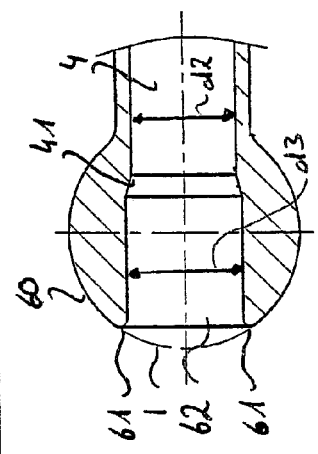

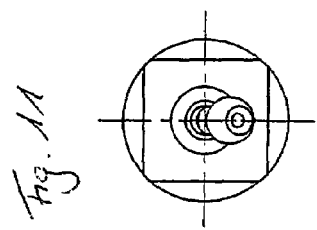
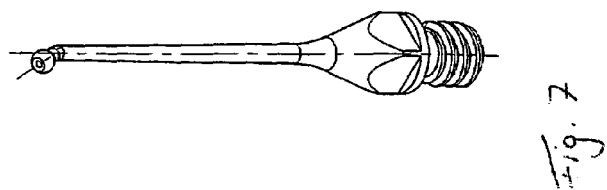
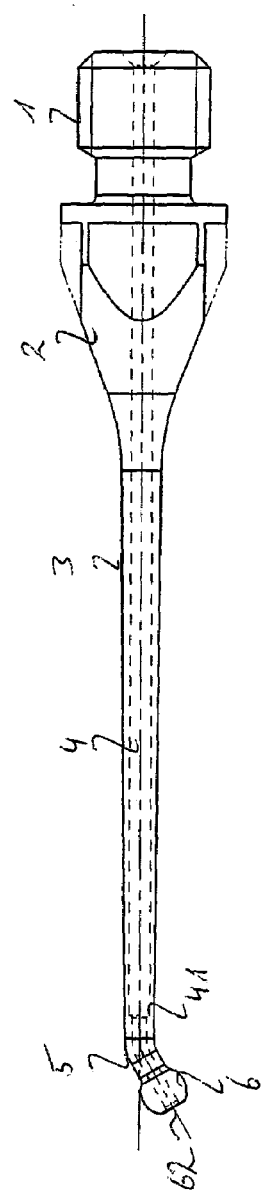
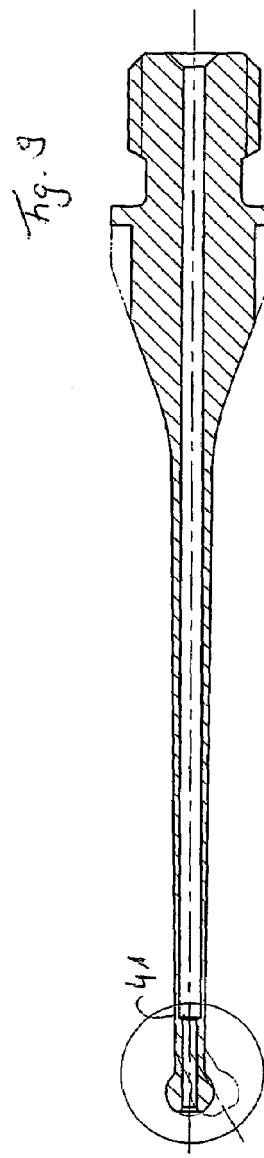
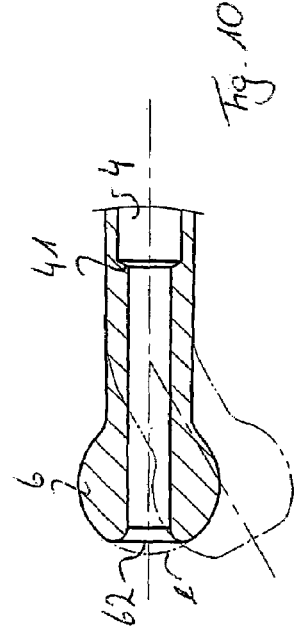

PHACOEMULSIFICATION NEEDLE

FIELD OF THE INVENTION

This invention relates to a phacoemulsification needle for an ultrasonic surgical instrument, the needle being designed for promoting cavitation in eye tissue and for the removal of fragmented lens from the eye.

BACKGROUND OF THE INVENTION

Phacoemulsification has become the preferred form of cataract, i.e. a cloudy eye lens, removal. One of the main advantages of phacoemulsification is, that only a small incision into the cornea or sclera of an eye is needed to remove the cataract. Furthermore, the removal of the cataract can be done very quickly. After the cataract is removed, an intraocular lens is inserted to replace the original lens.

The phacoemulsification technique uses a hand held microsurgical tool known as phacoemulsifier. This phacoemulsifier comprises a handpiece and a small diameter needle with a tip to be inserted into the small incision of the eye. The needle and therefore the tip are vibrated by an ultrasonic source. It breaks the cataract into small fragments and pieces, which are sucked out through the same tip in a controlled manner. The tip is therefore designed for emulsifying, fragmenting and/or cutting tissue and also comprises a central hollow bore or lumen for the suction or aspiration of the fragments.

During the procedure, an irrigation solution is introduced to maintain the pressure and to prevent the eye from collapsing. In order to introduce the irrigation solution, the needle is usually covered by a sleeve and the solution flows via the space between this sleeve and the needle. The solution is therefore also used to cool the tip, which is heating up during the phacoemulsification.

Usually, the needle and often the handpiece must be changed after the removal of the cataract nucleus in order to remove the residual cortex. It takes time to change the handpiece and the continuation of the surgery is disrupted.

U.S. Pat. No. 5,653,724 discloses a phacoemulsification needle which is angled to provide more comfortable ergonomic angle during phacoelmulsification and lens cortex removal. This angled needle is also considered to produce less heat when emulsifying the lens. Another angled phacoemulsification needle with a concentric sleeve is disclosed in U.S. Pat. No. 5,993,409.

Different shapes of phacoemulsification needles with slits, a second infusion hole and/or with increased outside diameter at the distal end of the needle body and the needles being surrounded by sleeves are described in U.S. Pat. No. 5,989,209, U.S. Pat. No. 6,159,175, EP-A-1'103'238, WO 00/74615 and US 2002/0099325.

Other techniques for cataract removal use laser energy to remove the cataract. A laser/aspiration probe is used for breaking and removing the lens. A separate infusion or irrigation probe is used for the irrigation solution.

SUMMARY OF THE INVENTION

It is an object of the invention to provide a phacoemulsification needle which can be used for the removal of the cataract nucleus as well as the residual cortex.

This object is achieved with a phacoemulsification needle comprising
a shaft,
a tip, disposed at a distal end of said shaft, said tip having a larger outer diameter than said shaft and
an aspiration lumen extending through said shaft and said tip, the tip having an opening communicating with said aspiration lumen,
wherein said tip has a ball-shaped surface and wherein the tip has a flat distal end comprising said opening.

This object can also be achieved with a phacoemulsification needle comprising
a shaft,
a tip, disposed at a distal end of said shaft, said tip having a larger outer diameter than said shaft and
an aspiration lumen extending through said shaft and said tip, the tip having an opening communicating with said aspiration lumen,
wherein said tip has a curved shape and wherein the tip has a distal end comprising said opening.

This object can also be achieved with a phacoemulsification needle comprising
a shaft,
a tip, disposed at a distal end of said shaft, said tip having a larger outer diameter than said shaft and
an aspiration lumen extending through said shaft and said tip, the tip having an opening communicating with said aspiration lumen,
wherein said tip has a curved shape, the tip comprising a distal end and at least two openings being arranged in the region of said distal end.

With this ball-shaped or curved tip design and the opening arranged at the distal end or the at least two openings being arranged in the region of said distal end, it is possible to remove both the cataract nucleus and the residual cortex.

This tip can be used for irrigation and aspiration without having to change the tip and therefore having the advantage that time can be saved. The tip can be used for irrigation and/or aspiration if desired. It can not only be used for phacoemulsification, but also for cortical removal and for polishing the capsule.

The needle according to the invention can be used with or without an irrigation sleeve.

In preferred embodiments, the tip has a ball-shaped, round, spherical, oval or smooth continuous curved shape.

In a preferred embodiment, the tip has at its distal end rounded edges. This avoids unwished damage of tissue. Due to the inventive shape of the tip, especially its broad and smooth spherical surface area of the tip, no damage to the posterior capsule can occure.

In a preferred embodiment, the tip comprises a slit extending in longitudinal direction of the needle. When a high vacuum setting is used with the phacoemulsifier, the anterior chamber, formed of a part of the lumen extending in the tip, becomes unstable when occlusion break occurs. In this case, small amount of irrigation fluid will continue to flow through the aspiration lumen. Furthermore, when occlusion surge occurs, the amount of surge can be reduced. Instead of the slit, an opening can be provided in a region adjacent to the tip.

The tip can comprise more than one opening of the lumen, these openings being arranged in the region of the distal end. In this case, the distal end can have instead of a flat shape a rounded one. This embodiment even increases the safety from rupturing the posterior capsule.

Further preferred embodiments of the invention are described in the dependent claims.

BRIEF DESCRIPTION OF THE DRAWINGS

The present invention will be more clearly understood with reference to the following detailed description of preferred embodiments, taken in conjunction with the accompanying drawings, in which FIG. 1 shows a perspective view of a needle according to the invention in a first embodiment;

FIG. 2 shows a side view of the needle according to FIG. 1;

FIG. 3 shows a longitudinal view of the needle according to FIG. 1;

FIG. 4 shows a magnified part of the needle tip according to FIG. 3;

FIG. 5 shows a front view of the needle according to FIG. 1;

FIG. 6 shows a front view of a needle according to a second embodiment;

FIG. 7 shows a perspective view of a needle according to the invention in a third embodiment;

FIG. 8 shows a side view of the needle according to FIG. 7;

FIG. 9 shows a longitudinal view of the needle according to FIG. 7;

FIG. 10 shows a magnified part of the needle tip according to FIG. 7;

FIG. 11 shows a front view of the needle according to FIG. 7;

DESCRIPTION OF THE PREFERRED EMBODIMENTS

Figure 15:
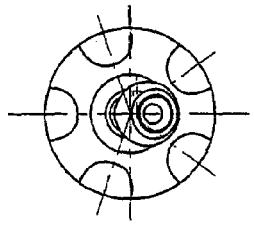
FIG. 15 shows a front view of the needle according to FIG. 12.
Figure 12:
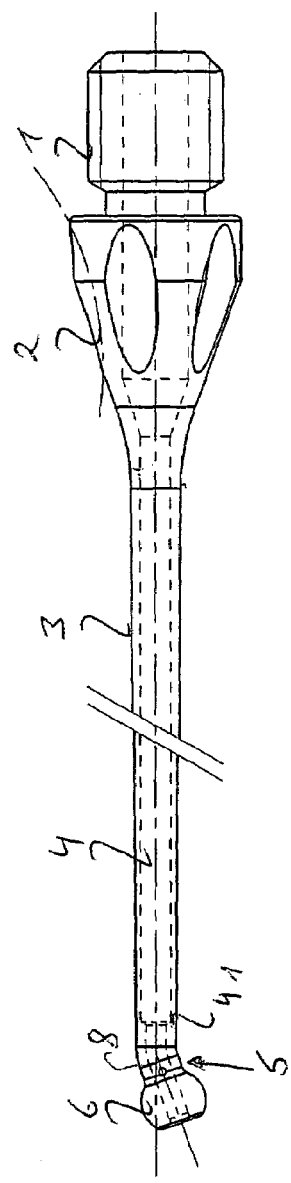
FIG. 12 shows a side view perspective view of a needle according to the invention in a fourth embodiment.
Figure 13:
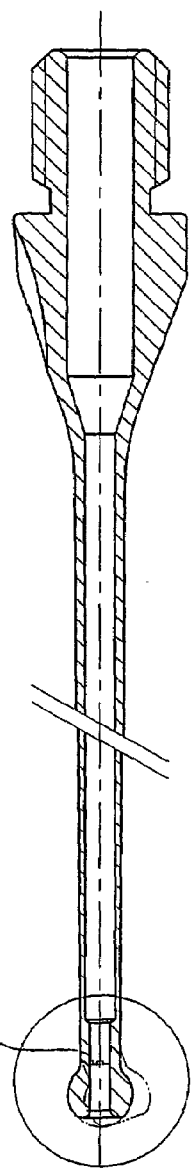
FIG. 13 shows a longitudinal view of the needle according to FIG. 12.
Figure 14:
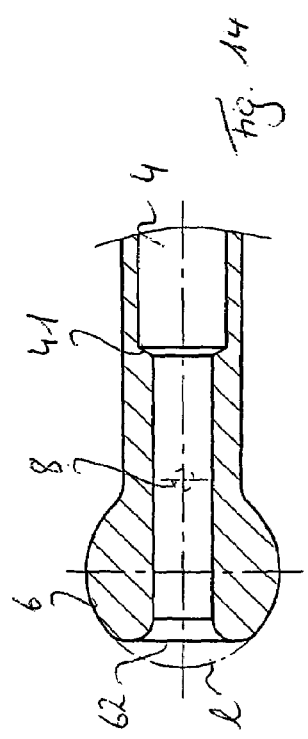
FIG. 14 shows a magnified part of the needle tip according to FIG. 13.

With reference to FIGS. 1 and 2, there is shown a phacoemulsification needle in accordance with the present invention. The needle may be formed from any conventional material as is known in the art for the manufacture of phacoemulsification needles. Usually, it is made of titanium.

The needle comprises, starting with its proximal end and ending with its distal end, a threaded portion 1, a hub 2, a shaft 3 and a tip 6 having at least one opening. The threaded portion 1 and the hub 2 are used to fix the needle on a ultrasonic device of the phacoemulsification handpiece (not shown) in order to couple ultrasonic energy to the needle.

The needle further comprises, with reference to FIGS. 3 and 4, an aspiration lumen 4 extending through the whole longitudinal length of the needle shaft 3 and communicating with the opening of the tip for aspiration of irrigation fluid and therefore for removal of fragments and pieces of the cataract nucleus and residual cortex. Preferably, the lumen 4 comprises a first step 40 in the region of the hub 2 neighboring the shaft 3. The first diameter d1 of the part of the lumen extending within the hub 2 is therefore larger than the second diameter d2 of the lumen part extending within the shaft 2. This first step 40 has preferably a conical shape.

A second step 41, which has preferably also a conical shape, is located within the tip 6, wherein the second diameter d2 is smaller than a third diameter d3 of the lumen part extending within the shaft 2. This diameter d3 corresponds with the diameter of the opening of the tip 6.

With exception of the steps 40, 41, the lumen 4 preferably has throughout its whole length the same size. In particular the lumen part extending in the tip 6 has a cylindrical shape.

The shaft 3 is preferably angled. However, it is also possible to have a rectilinear shaft. In the here described embodiment however, the shaft 3 comprises an angled portion 5 neighboring the tip 6. The aspiration lumen 4 within the tip extends in a rectilinear way.

The tip 6 as shown in FIG. 5 as well and which is arranged at the distal end of the shaft 3, has a larger outer diameter D2 than the outer diameter D1 of the shaft 3. Furthermore, it has a ball-shaped surface 60 and a flat distal end 62. In this preferred embodiment, the flat distal end 62 is formed by the opening. However, the opening can also be smaller, so that the end face of the tip 6 is flat. In the here described embodiment however, the end face is formed by rounded blunt edges 61. The above mentioned second step 41 is preferably located in the tip 6 itself at a distance to the transition of the ball-shaped surface 60 to the surface of the shaft 3. In FIG. 4, a curved line 1 is shown at the distal end of the tip 6. This line 1 is just an auxiliary line showing that, with exception of the flat distal end, the tip has a completely spherical surface.

A preferred embodiment of the inventive needle has an outer diameter D2 for the shaft 2 of approximately 1.06 mm, an outer diameter D1 of the tip 6 of approximately 1.6 mm, a first diameter d1 of the lumen 4 of approximately 1.32 mm, a second diameter d2 of approximately 0.72 mm, a third diameter d3 of approximately 0.8 mm, a length L of the tip 5 (extending up to the curved line 1) of approximately 1.46 mm and a distance X from the curved line 1 to the second step 41 of approximately 1.05 mm. The radius of curvature of the rounded edges 61 is approximately 0.15 mm, the angle of the first step 40 approximately 34° and the angle of the second step 41 approximately 30°. The angle γ between shaft 3 and tip 4 lays between 10 and 15°. Here it is approximately 15°. The total length of the needle up to the curved line 1 is approximately 30.15 mm.

FIG. 6 shows a second preferred embodiment of the needle according to the invention. The needle is built in the same way as the needle according to the previously described figures. The only difference is, that this tip 6 comprises a slit 7 extending in longitudinal direction of the needle, which communicates with the aspiration lumen 4.

FIGS. 7 to 11 show a third embodiment of the needle according to the invention. The threaded portion 1 is slightly shorter than the one shown in FIG. 2. The hub 2 has not a generally circular cross section but a rectangular, preferably a quadratic one. This hub 2 and this threaded portion 1 can also be used with the tips disclosed in the other embodiments and the hup and threaded portion disclosed in FIG. 2 can be used with this tip.

The aspiration lumen 4 extending through the needle shaft 3 comprises a second step 41 like the one shown in FIG. 1. However, this second step 41 is arranged is located outside of the tip 6. This second step 41 is in this case preferably arranged behind the angled portion 5. If the shaft 3 is rectilinear, the second step 41 is preferably arranged in a distance behind the tip 6 which has approximately the same length as the tip 6. This step 41 reduces the cross section of the lumen 4. In addition, no first step is located within the hub 2.

This second step 41 however can also be arranged in the tip 6. Furthermore, instead of this step, the second step according to FIG. 2 can be used. The embodiment according to FIG. 2 can also have the second step 41 being arranged in the shaft 3 instead in the tip 6, wherein the second step 41 can reduce or increase the cross section of the opening at the distal end 62. Furthermore, this second step can, but must not be conical.

Since the opening a the distal end 62 according to this third embodiment, the tip 6 has a curved shape, which is slightly different to the one of the first embodiment. The distal end 62 is less flat and the curved line 1 is shorter.

FIGS. 12 to 15 show a fourth embodiment of the invention. In this embodiment, an opening 8 in the shape of a circular hole is located behind the tip 6. If the shaft 3 is angled, this opening 8 is preferably located in the angled portion 5. This opening 8 communicates with the aspiration lumen 4. Like the slit 7, this opening 8 helps when the anterior chamber, formed of a part of the lumen extending in the tip, becomes unstable when occlusion break occurs. In this case, small amount of irrigation fluid will continue to flow through the aspiration lumen. Furthermore, when occlusion surge occurs, the amount of surge can be reduced by this slit 7 or this opening 8. This fourth embodiment can also comprise instead of the opening 8 the slit 7 shown in FIG. 6.

Figure 16:
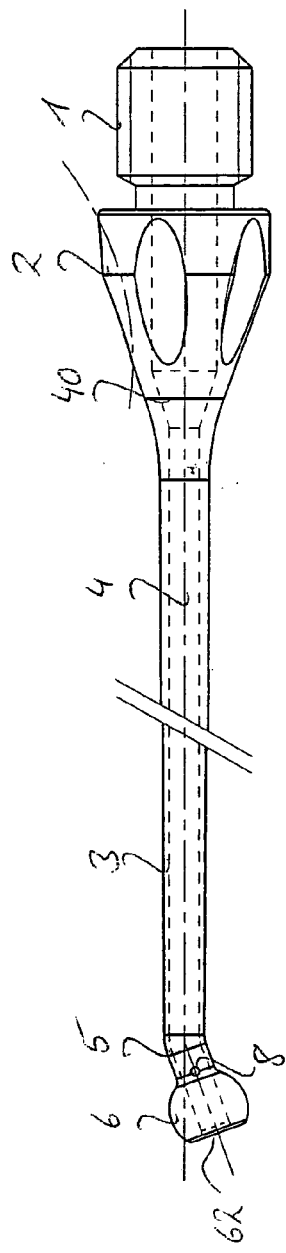
FIG. 16 shows a side view of a needle according to the invention in a fifth embodiment.
Figure 17:
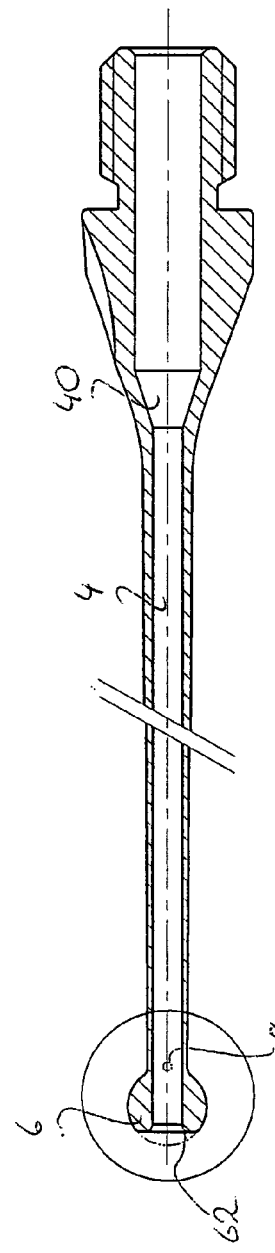
FIG. 17 shows a longitudinal of the needle according to FIG. 16.
Figure 18:
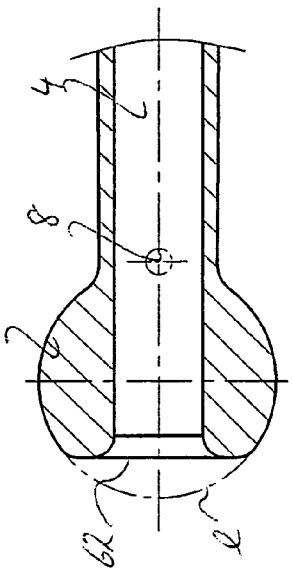
FIG. 18 shows a magnified part of the needle tip according to FIG. 17.

FIGS. 16 to 18 show a fifth embodiment of the invention. Here, there exists no second step 41, neither in the shaft 3 nor in the tip 6. This embodiment can be used with the opening 8 or the slit 7 or without any of them. Furthermore, any of the above mentioned embodiments can comprise the opening 8 as well as the slit 7.

Figure 21:
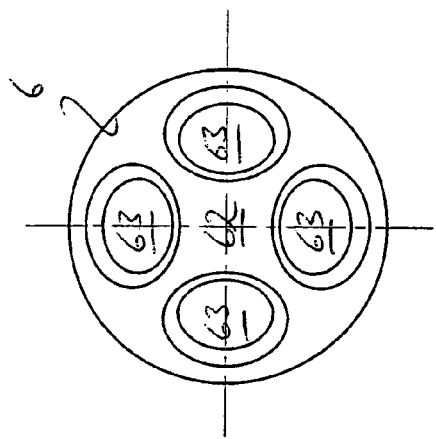
FIG. 21 shows a front view of the needle according to FIG. 19.
Figure 19:
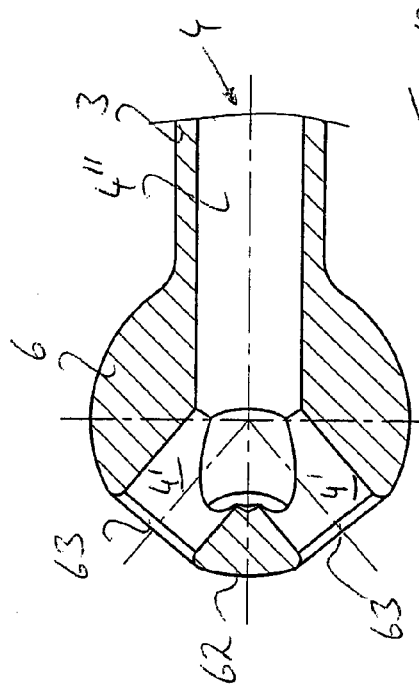
FIG. 19 shows a longitudinal view of a needle according to the invention in a sixth embodiment.
Figure 20:
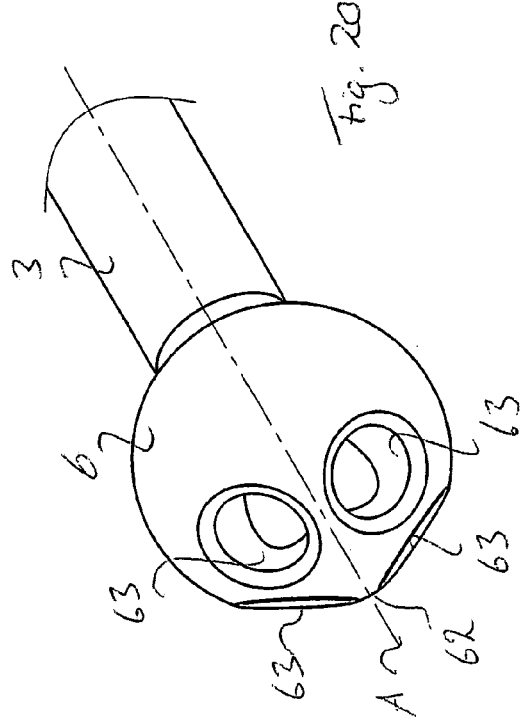
FIG. 20 shows a perspective view of the needle according to FIG. 19.

A sixth embodiment is shown in the FIGS. 19 to 21. The first and second steps 40 and 41 can be arranged or being nonexistent as described in any of the previous embodiments. Furthermore, this embodiment can comprises an opening 8 and/or a slit 7 or none of them. The tip 6 of this embodiment still has a curved shaped. This embodiment however comprises instead of the flat distal end 62 being defined by a distal opening of the lumen 4 at least two openings 63 of the lumen 4 being arranged in the region of the distal end 62. Here, we have such four openings 63. However, there can also be three, five or more openings. Preferably, the are arranged in a symmetrical manner around the longitudinal axis A defined by the shaft 3. These openings 63 have like the single opening of the other embodiments blunt or rounded edges 61. In order to communicate with these openings 63, the lumen 4 is divided into sublumens 4', each sublumen 4' ending in one of the mentioned openings 63. This division is preferably made only in the tip 6. If a slit 7 or an opening 8 are provided, they can be arranged in the region of the undivided lumen 4" or the different sublumens 4' can comprise a subslit each ending in a common slit 7 or each sublumen 4" can comprise an one opening 8.

In the above description, the shape of the tip was normally described a ball-shaped. However, the tip 6 can have a generally curved shape, preferably a ball-shaped, round, spherical, oval or smooth continuous curved shape.

The needle according to the invention can be used for the ultrasonic part of the phacoemulsification procedure, i.e. for the removal of the cataract nucleus, as well as for the irrigation/aspiration part of the procedure, i.e. for the removal of the residual tissue.

LIST OF REFERENCE NUMBERS 1 threaded portion
2 hub
3 shaft
4 lumen
4' sublumen
4" undivided lumen
40 first step
41 second step
5 angled portion
6 tip
60 ball-shaped surface
61 rounded edges
62 flat distal end
63 opening of the lumen
7 slit
8 opening
d1 first diameter
d2 second diameter
d3 third diameter
D2 outside diameter of the shaft
D1 outside diameter of the tip
L length of the tip
l curved line
X distance
γ angle
A longitudinal axis

The invention claimed is:

1. A phacoemulsification needle for removing a cataract from an eye, said needle comprising:
    a shaft having a longitudinal axis,
    a threaded portion and a hub, disposed at a proximal end of the shaft, for fixing the needle to an ultrasonic device;
    a metal tip, disposed at a distal end of said shaft, having:
        an opening, disposed in a flat distal terminus perpendicular to the longitudinal axis of the shaft,
        an essentially completely spherical surface except for the terminus, and
        a larger outside diameter than said shaft; and
    an aspiration lumen, extending through said shaft and said tip, in communication with the opening in the tip,
    wherein said tip includes rounded edges disposed around said opening and extending to said aspiration lumen.

2. The needle according to claim 1, wherein said flat distal end is formed by said opening.

3. The needle according to claim 1, wherein the part of said aspiration lumen extending within the tip is rectilinear.

4. The needle according to claim 1, wherein the needle is angled.

5. The needle according to claim 1, wherein said opening has a larger diameter than the part of the aspiration lumen extending within said shaft.

6. The needle according to claim 1, wherein said aspiration lumen comprises a step within the tip.

7. The needle according to claim 1, wherein said opening has a diameter of approximately 0.8 mm.

8. The needle according to claim 1, wherein said rounded edges have a radius of curvature of approximately 0.15 mm.

9. The needle according to claim 1, wherein said tip comprises a slit extending in longitudinal direction of the needle and communicating with said aspiration lumen.

10. The needle according to claim 1, wherein the metal tip is made of titanium.

11. A phacoemulsification needle for removing a cataract from an eye, comprising:
a shaft having a longitudinal axis,
a threaded portion and a hub, disposed at a proximal end of the shaft, for fixing the needle to an ultrasonic device;
a metal tip, disposed at a distal end of said shaft, having:
an opening disposed in a flat distal terminus perpendicular to the longitudinal axis of the shaft,
a smooth, continuous curved shape except for the terminus, and
a larger outside diameter than said shaft; and
an aspiration lumen, extending through said shaft and said tip, in communication with the opening in the tip,
wherein said tip includes rounded edges disposed around said opening and extending to said aspiration lumen.

12. The needle according to claim 11, wherein said flat distal end is formed by said opening.

13. The needle according to claim 11, wherein the part of said aspiration lumen extending within the tip is rectilinear.

14. The needle according to claim 11, wherein the needle is angled.

15. The needle according to claim 11, wherein said opening has a larger diameter than the part of the aspiration lumen extending within said shaft.

16. The needle according to claim 11, wherein said opening has a smaller diameter than the part of the aspiration lumen extending within said shaft.

17. The needle according to claim 11, wherein said aspiration lumen comprises a step within the tip.

18. The needle according to claim 11, wherein said aspiration lumen comprises a step within the shaft.

19. The needle according to claim 11, wherein said opening has a diameter of 0.3 mm to 0.8 mm.

20. The needle according to claim 11, wherein said rounded edges have a radius of curvature of 0.1 mm to 0.15 mm.

21. The needle according to claim 11, wherein said tip comprises a slit extending in longitudinal direction of the needle and communicating with said aspiration lumen.

22. The needle according to claim 11, wherein said shaft comprises an opening extending through its surface, the opening communicating with said aspiration lumen.

23. The needle according to claim 11, wherein the metal tip is made of titanium.

24. A phacoemulsification needle for removing a cataract from an eye, comprising:
a shaft,
a threaded portion and a hub, disposed at a proximal end of the shaft, for fixing the needle to an ultrasonic device;
a metal tip, disposed at a distal end of said shaft, having:
a distal terminus and at least two openings arranged near the terminus,
an overall smooth, continuous curved shape, and
a larger outside diameter than said shaft; and
an aspiration lumen, extending through said shaft and said tip, in communication with the openings near the terminus,
wherein said tip includes rounded edges disposed around said at least two openings and extending to said aspiration lumen.

25. The needle according to claim 24, wherein the tip comprises four openings.

26. The needle according to claim 24, wherein the distal end has a curved surface.

27. The needle according to claim 24, wherein said lumen is divided into sublumens, each sublumen ending in one of said openings.

28. The needle according to claim 27, wherein said sublumens are arranged in an angle to said lumen and to a longitudinal axis of the shaft.

29. The needle according to claim 28, wherein the angle is approximately 45°.

30. The needle according to claim 27, wherein the sublumens extend only in the tip.

31. The needle according to claim 24, wherein the needle is angled.

32. The needle according to claim 24, wherein the metal tip is made of titanium.

33. A method of phaco-emulsification, comprising:
providing a needle having:
a shaft having a longitudinal axis;
a tip, disposed at a distal end of said shaft, having:
an opening, defined by a rounded edge, disposed in a flat distal terminus perpendicular to the longitudinal axis of the shaft,
an essentially completely spherical surface except for the terminus, and
a larger outside diameter than said shaft, and
an aspiration lumen, extending through said shaft and said tip, in communication with the opening in the tip;
inserting said tip in an eye having a cataract;
vibrating said tip with substantially ultrasonic vibration;
breaking substantially said cataract into pieces with said tip; and
aspirating substantially said pieces through said aspiration lumen.

34. The method according to claim 33, wherein said needle includes a threaded portion and a hub, disposed at a proximal end of the shaft, for fixing the needle to an ultrasonic device.

35. A method of phaco-emulsification, comprising:
providing a needle having:
a shaft having a longitudinal axis;
a tip, disposed at a distal end of said shaft, having:
an opening, defined by a rounded edge, disposed in a flat distal terminus perpendicular to the longitudinal axis of the shaft,
a smooth, continuous curved surface except for the terminus, and
a larger outside diameter than said shaft, and
an aspiration lumen, extending through said shaft and said tip, in communication with the opening in the tip;
inserting said tip in an eye having a cataract;
vibrating said tip with substantially ultrasonic vibration;
breaking substantially said cataract into pieces with said tip; and
aspirating substantially said pieces through said aspiration lumen.

36. The method according to claim 35, wherein said needle includes a threaded portion and a hub, disposed at a proximal end of the shaft, for fixing the needle to an ultrasonic device.

37. A method of phaco-emulsification, comprising: providing a needle having:
a shaft;

a tip, disposed at a distal end of said shaft, having:
  a distal terminus and at least two openings, defined by rounded edges.
    arranged near the terminus,
    an overall smooth, continuous curved shape, and
    a larger outer diameter than said shaft, and
an aspiration lumen, extending through said shaft and said tip, in communication
with the openings in the tip;
inserting said tip in an eye having a cataract;
vibrating said tip with substantially ultrasonic vibration;
breaking substantially said cataract into pieces with said tip; and
aspirating substantially said pieces through said aspiration lumen.

38. The method according to claim 37, wherein said needle includes a threaded portion and a hub, disposed at a proximal end of the shaft, for fixing the needle to an ultrasonic device.

* * * * *